United States Patent [19]

Mahurkar

[11] Patent Number: 4,568,329

[45] Date of Patent: Feb. 4, 1986

[54] DOUBLE LUMEN CATHETER

[76] Inventor: Sakharam D. Mahurkar, 6171 N. Sheridan, Ste. 1112, Chicago, Ill. 60660

[21] Appl. No.: 656,601

[22] Filed: Oct. 1, 1984

Related U.S. Application Data

[63] Continuation of Ser. No. 356,081, Mar. 8, 1982, abandoned.

[51] Int. Cl.[4] .................. A61M 1/03; A61M 25/00
[52] U.S. Cl. ........................... 604/43; 604/280
[58] Field of Search ...................... 604/43–45, 604/280

[56] References Cited

U.S. PATENT DOCUMENTS

| | | | |
|---|---|---|---|
| D. 250,349 | 11/1978 | McFarlane | D24/54 |
| D. 256,617 | 8/1980 | Clemens | D24/54 |
| D. 272,651 | 2/1984 | Mahurkar . | |
| 998,339 | 7/1911 | Hollins | 27/24 A |
| 1,290,647 | 1/1919 | Nyvall | 128/214 R X |
| 2,175,726 | 10/1939 | Gebauer | 128/349 B |
| 2,474,665 | 6/1949 | Guarino | 128/DIG. 3 |
| 2,564,977 | 8/1951 | Hsi Hu | 128/214 X |
| 2,590,895 | 4/1952 | Scarpellino | 128/221 |
| 2,625,932 | 1/1953 | Salisbury | 128/214.2 |
| 3,324,853 | 6/1967 | Czorny et al. | 128/214.4 |
| 3,463,152 | 8/1969 | Sorenson | 128/214.4 |
| 3,550,591 | 12/1970 | MacGregor | 128/214.4 |
| 3,804,097 | 4/1974 | Rudie | 128/350 R |
| 4,027,668 | 6/1977 | Dunn | 128/214 R |
| 4,096,860 | 6/1978 | McLaughlin | 128/214.4 |
| 4,098,275 | 7/1978 | Consalvo | 128/221 X |
| 4,099,528 | 7/1978 | Sorenson et al. | 128/214.4 |
| 4,134,402 | 1/1979 | Mahurkar | 128/221 X |
| 4,144,884 | 3/1979 | Tersteegen et al. | 128/214.4 |
| 4,180,068 | 12/1979 | Jacobsen et al. | 128/214 R |
| 4,202,332 | 5/1980 | Tersteegen et al. | 128/221 X |
| 4,203,436 | 5/1980 | Grimsrud | 128/214 R |
| 4,270,535 | 7/1981 | Bogue et al. | 128/214.4 |
| 4,336,036 | 6/1982 | Leeke et al. | 128/214 R X |
| 4,385,631 | 5/1983 | Uthmann | 604/284 |
| 4,403,983 | 3/1983 | Edelman et al. | 604/43 |
| 4,451,252 | 5/1984 | Martin | 604/43 |

FOREIGN PATENT DOCUMENTS

| | | | |
|---|---|---|---|
| 834211 | 2/1976 | Belgium | 128/221 |
| 1092927 | 1/1981 | Canada | 604/43 |
| 50089 | 8/1982 | Canada . | |
| 36642 | 9/1981 | European Pat. Off. | 604/43 |
| 2259865 | 6/1974 | Fed. Rep. of Germany | 128/221 |
| 19346 | 6/1982 | Fed. Rep. of Germany . | |
| 592193 | 4/1925 | France | 128/214.2 |
| 821344 | 4/1982 | France . | |
| 55-88771 | 7/1980 | Japan | 128/348 |
| 1419702 | 12/1975 | United Kingdom | 128/221 |
| 1006219 | 3/1983 | United Kingdom . | |

OTHER PUBLICATIONS

McIntosh et al., "Double Lumen Catheter", *J.A.M.A.*, Feb. 21, 1959, pp. 137/835–138/836.

*Dorland's Illustrated Medical Dictionary*, 25th Ed., W. B. Saunders Co., Philadelphia, 1974, p. 274.

Brenner & Rector, *The Kidney*, vol. III, W. B. Saunders Co., Philadelphia, 1976, p. 164.

*ASAIO Abstracts*, vol. 5, 22nd Annual Meeting, San Francisco, Calif., Apr. 1–3, 1976, p. 52.

Tohoku, J., "Single Two-Luman Cannula Dialysis", Aug., 1974.

*Primary Examiner*—Dalton L. Truluck
*Attorney, Agent, or Firm*—Leydig, Voit & Mayer, Ltd.

[57] ABSTRACT

A double lumen catheter has an elongated tube with a proximal first cylindrical portion having an internal divider to define a pair of discrete lumens including a shorter lumen opening at approximately the distal end of the first cylindrical portion, and a longer lumen opening at the distal end of the elongated tube. The longer lumen is further defined by a distal second cylindrical portion of the elongated tube which has a diameter substantially less than the diameter of the first proximal cylindrical portion of the elongated tube. To promote insertion and to perform a dilator function, the distal end of the tube has a smooth conical tapered tip that smoothly merges with the distal second cylindrical portion of the elongated tube. Preferably, the lumens are "D" shaped in the first cylindrical portion, a plurality of outlet holes are provided in the vicinity of the conical tapered tip, and the shorter lumen opens at an aperture having a bevel. The double lumen catheter is particularly advantageous when a tunneling procedure or blind technique must be used, for example, to reach a vein under the collar bone or neck.

8 Claims, 6 Drawing Figures

U.S. Patent     Feb. 4, 1986     4,568,329
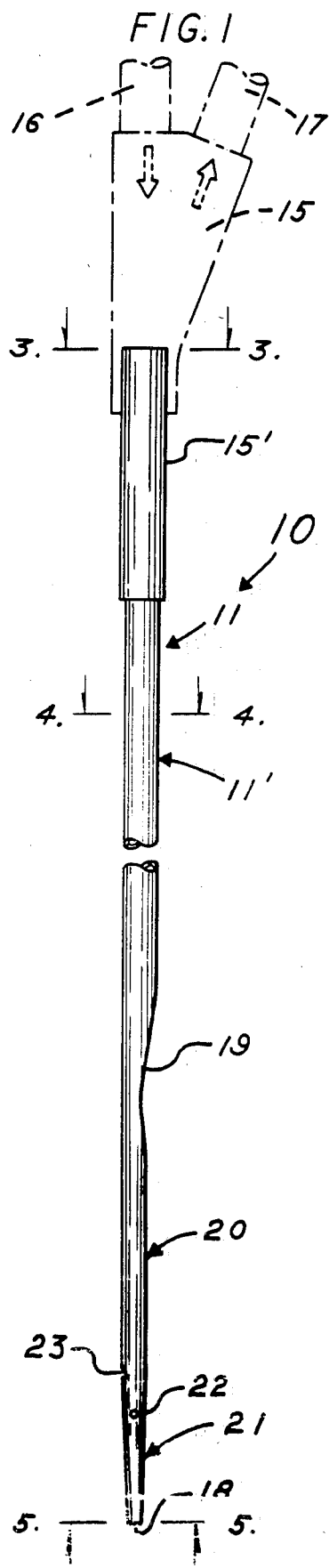
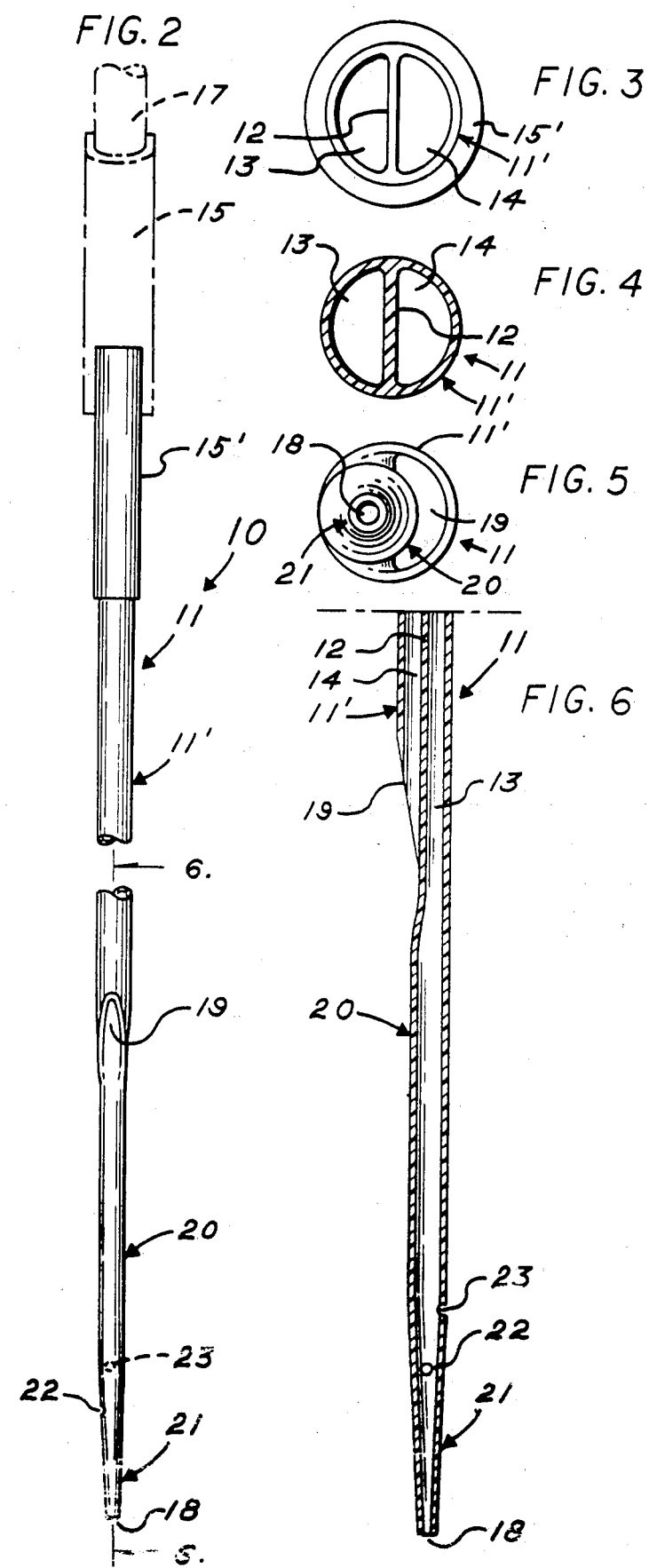

DOUBLE LUMEN CATHETER

RELATED APPLICATIONS

The present application is a continuing application of Ser. No. 356,081 filed Mar. 8, 1982, which is abandoned.

BACKGROUND OF THE INVENTION

1. Field of the Invention

The present invention relates to surgical instruments for withdrawing fluids from or introducing fluids into a cavity of the body.

2. Description of the Related Art (Information Disclosure Statement Incorporated Into The Specification per 37 C.F.R. §1.97(a))

As is well known, a catheter is a tubular, flexible, surgical instrument for withdrawing fluids from (or introducing fluids into) a cavity of the body. A double-current catheter is a catheter having two channels; one for injection and one for removal of fluid. *Dorlan's Illustrated Medical Dictionary Twenty-Fifth Edition* (W. B. Saunders, Philadelphia 1974), p. 274. As is well known, a double-current catheter is used for removing blood from a fistula or vein for processing in a dialysis machine and returning the processed blood back to the fistula or vein. A double-current catheter suitable for this purpose is disclosed in Mahurkar, U.S. Pat. No. 4,134,402 issued Jan. 16, 1979. Mahurkar U.S. Pat. No. 4,134,402 discloses a double lumen continuous flow hemodialysis needle and cannula having contiguous lumens of different lengths formed by dividing a unitary straight tube, the shorter lumen acting as a blood intake lumen and the longer acting as a blood return lumen. Semi-circular lumens provide a minimal resistance to blood flow resulting in a smaller but highly efficient catheter in comparison to a coaxial double-current catheter. Hemodialysis requires, for example, a blood flow rate of about 200 ml/min or more and flow resistance less than about 100 mm of mercury.

There are numerous other United States Patents disclosing double-current catheters for hemodialysis and evidencing a long-felt need for a small, functionally efficient catheter having a minimum of insertion trauma and potential for clotting. McLaughlin, U.S. Pat. No. 4,096,860 issued June 27, 1978 discloses a coaxial hemodialysis catheter said to allow a step enlargement of the opening of a blood vessel to avoid tearing and rupture of the side walls. A simultaneous flow device incorporates a hub with an extension conduit and a valve therein for receipt of a needle therethrough. The extension conduit is of sufficient size to allow the passage of the needle therethrough adjacent the interior side walls thereof with an attendent extension thereof from its opening. The needle with the extension conduit is adapted for combined insertion within a blood vessel, after which it can be withdrawn while the valve prevents the backflow of blood through the axial passage of the hub. A coaxial flow device can then be inserted within the hub conduit.

Sorenson et al., U.S. Pat. No. 4,099,528 issued July 11, 1978 discloses a coaxial double lumen cannula mounted upon a hub and having a central stylet needle for penetrating a patient's vein and which is retractable after penetration.

Grimsrud, U.S. Pat. No. 4,203,436 issued May 20, 1980 discloses a hollow hypodermic needle with a divider for providing a first channel for removal of blood for treatment from a punctured blood vessel and a second channel for returning the treated blood to the blood vessel.

Uthmann, U.S. Pat. No. 4,385,631 issued May 31, 1983 discloses a hemodialysis catheter for puncturing blood vessels which includes a section insertable through a puncture opening into a blood vessel and a hose line following thereafter.

Jacobson et al., U.S. Pat. No. 4,180,068 issued Dec. 25, 1979 discloses a double-current hemodialysis catheter comprising a primary tube and an internal divider which also functions as a trocar and valve. The primary tube has a side opening for receiving blood and a central opening at the distal end of the primary tube. The internal divider includes a cutting end which protrudes from the distal opening when the divider is longitudinally moved to an insert position. In the insert position, blood flow is blocked.

Mahurkar, U.S. Pat. No. Des. 272,651 issued Feb. 14, 1984 discloses a double lumen catheter having an outlet lumen which has an opening at the tip of the catheter and a shorter inlet lumen which terminates in a bevel substantially displaced from the tip.

SUMMARY OF THE INVENTION

The primary object of the invention is to provide an efficient dual lumen catheter having minimal insertion trauma and a minimal potential for clotting.

Another object of the invention is to provide a dual lumen catheter which is an effective dilator for soft tissue and veins.

BRIEF DESCRIPTION OF THE DRAWINGS

Other objects and advantages of the invention will become apparent from the following detailed description and the accompanying drawings, in which:

FIG. 1 is a side elevational view showing a preferred embodiment of the double lumen catheter according to the invention;

FIG. 2 is a rear elevational view of the catheter illustrated in FIG. 1;

FIG. 3 is an end view of the solid line portion of the catheter illustrated in FIG. 1 as seen along line 3—3 thereof;

FIG. 4 is a sectional view of the catheter illustrated in FIG. 1 as taken along line 4—4 thereof;

FIG. 5 is an end view partly in section of the catheter illustrated in FIG. 1 as seen along line 5—5 thereof; and FIG. 6 is a sectional view of the bottom portion of the catheter illustrated in FIG. 2 as taken along line 6—6 thereof.

While the invention will be described in connection with a certain preferred embodiment, it will be understood that it is not intended to limit the invention to that particular embodiment. On the contrary, it is intended to cover all alternatives, modifications, and equivalents as may be included within the spirit and scope of the invention as defined by the appended claims.

DETAILED DESCRIPTION OF THE PREFERRED EMBODIMENT

Turning now to the drawings, FIGS. 1, 2 and 5 show the various external views of a preferred embodiment of a double lumen catheter, generally designated 10, in accordance with the present invention. As is conventional for a double-current catheter, the double lumen catheter 10 has an elongated hollow tube 11 which is inserted into a cavity of the body such as a fistula or vein. The tube 11 is circular in cross section over a proximal first cylindrical portion 11', as specifically shown in FIG. 4. The first proximal portion 11' has an internal planar divider 12 defining a return lumen 13 and an inlet lumen 14 within the interior of the hollow tube 11. The lumens 13 and 14 are semicircular or "D" shaped which minimizes resistance to fluid flow. As is conventional for this type of dual lumen construction, the planar divider 12 extends axially along the tube 11 from a branching connector 15. The branching connector 15 connects the distal end portions of the return lumen 13 and the inlet lumen 14 to respective fluid return and inlet lines 16 and 17 which are, for example, respective venous and arterial lines of a dialysis circuit. This preferred direction of fluid circulation is indicated by dashed arrows in FIG. 1. The branching connector 15 includes a coaxial sleeve 15' at the junction of the tube 11 and the connector 15. The sleeve 15' acts as a strain relief and also prevents kinking of the tube 11 at the junction.

The hollow tube 11 includes openings or apertures at the distal end portions of the lumens 13, 14 to permit the flow of fluid between a body cavity (not shown) and the lumens. The return lumen 13 extends along the entire length of the tube 11 to an aperture or opening 18 at the distal end or tip of the tube 11 as is more clearly shown in FIG. 6. The inlet lumen 14 is shorter than the return lumen 13 and terminates at its distal end at an aperture or opening 19 at approximately the distal end of the proximal first cylindrical portion 11'. This inlet opening 19 is substantially displaced from the return aperture 18 at the distal end of the tube.

In accordance with an important aspect of the invention, at least one of the lumens is elongated and cylindrically deformed at its end to facilitate insertion. As shown in FIGS. 1 and 6, the inlet opening 19 is defined by a bevel rising at its distal end from the planar divider 12 and terminating at its proximal end on the outer periphery of the first cylindrical portion 11' of the tube 11. Thus, the intersection of the plane of the bevel with the body of the first cylindrical portion 11' is half of an ellipse which partially encircles the inlet opening 19 as is evident in FIG. 2.

As shown in FIG. 6, the catheter 10 has a distal second cylindrical portion 20 extending from the inlet opening 19 to the return opening 18 and enclosing the return lumen 13. As is further evident in FIG. 5, the distal second cylindrical portion 20 has a diameter substantially exceeding one-half but less than a full diameter of the proximal first cylindrical portion 11' of the catheter 10. In the vicinity of the inlet opening 19 the divider 12 merges with approximately one-half of the peripheral wall of the distal second cylindrical portion 20. This preferred geometrical shape and relative size insures unrestricted blood flow and minimizes clotting yet also reduces insertion trauma. The distal second cylindrical portion 20 smoothly merges with the proximal first cylindrical portion 11' so that the outer circumference of the catheter 11, corresponding to the size of the aperture in the blood vessel into which the catheter is inserted, gradually increases.

Potential insertion trauma and kinking are further minimized by providing a conical tapered tip 21 at the distal end portion of the distal second cylindrical portion 20. Due to the reduced internal diameter of the return lumen 18 in the region of the conical tapered tip 21, a plurality of holes 22, 23 are provided in the region of the conical tapered tip to lower the resistance to blood flow out of the return lumen 13.

It is readily apparent to persons of ordinary skill in the art that the tube 11 of the catheter 10 as shown in FIG. 6 is easily formed from thermoplastic material. Specifically, the distal second cylindrical portion 20 is integrally formed from the tube 11 initially having a uniform cross-section as shown in FIG. 4 along its entire length. The tube 11 is deformed by the use of internal and external mandrels and the application of heat by any number of conventional means such as RF forming, thermal forming, or infra-red forming. The bevel at the inlet opening 19 is, for example, first cut and one-half of the outer wall of the tube 11 is removed from the inlet opening to the distal end of the tube. Then, an internal mandrel is inserted in the return lumen 13 at the distal end of the tube 11 to form the cylindrical geometry of the distal second cylindrical portion 20. Finally an inner mandrel is inserted in the return lumen 13 at the proximal end of the tube 11 to form the conical tapered tip 21 in cooperation with an external mandrel.

For use in hemodialysis, the double lumen catheter 10 is introduced in the direction of blood flow in a large vein over a hypodemic needle or Seldinger's guide wire, or through a sheath as is conventional. The inlet opening 19 on the blood inlet lumen 14 draws the blood for processing and the processed blood is returned through the return lumen 13 and out through the holes 18, 22, 23 to return the blood upstream into circulation. As was described above, the geometrical properties of the double lumen catheter as shown in the drawing figures insure that insertion trauma and the possibility of kinking and clotting are minimized during hemodialysis.

What is claimed is:

1. A double lumen catheter having an elongated tube with a proximal first cylindrical portion enclosing first and second lumens separated by an internal divider, the proximal end of said elongated tube connecting to two separate connecting tubes communicating with the respective first and second lumens for the injection and removal of fluid, the first lumen extending from the proximal end of said elongated tube to a first opening at the distal end of said elongated tube, and the second lumen extending from the proximal end of said elongated tube to a second opening at approximately the distal end of said first cylindrical portion, wherein the improvement comprises;

said elongated tube having at its distal end a smooth conical tapered tip that smoothly merges with a second cylindrical portion of said elongated tube, and said second cylindrical portion enclosing the first lumen from the conical tapered tip to approximately the location of said second opening, wherein said second cylindrical portion has a diameter substantially greater than one-half but substantially less than a full diameter of said first cylindrical portion.

2. The double lumen catheter as claimed in claim 1, wherein said divider in said first cylindrical portion is planar and merges with approximately one-half of the peripheral wall of said second cylindrical portion.

3. The double lumen catheter as claimed in claim 2, wherein the lumens are "D" shaped in cross-section in the region of said first cylindrical portion, and said second opening is defined by a bevel rising at its distal end from the planar divider and terminating at its proximal end on the outer periphery of the first cylindrical portion.

4. The double lumen catheter as claimed in claim 1, wherein the lumens are "D" shaped in cross-section in the region of said first cylindrical portion.

5. The double lumen catheter as claimed in claim 1, wherein the elongated tube is provided with a plurality of holes in the region of the conical tapered tip.

6. The double lumen catheter as claimed in claim 1, wherein said first cylindrical portion of the elongated tube smoothly merges with said second cylindrical portion of the elongated tube.

7. A double lumen catheter having an elongated tube with a proximal first cylindrical portion enclosing first and second lumens separated by an internal divider, the proximal end of said elongated tube connecting to two separate connecting tubes communicating with the respective first and second lumens for the injection and removal of fluid, the first lumen extending from the proximal end of said elongated tube to a first opening at the distal end of said elongated tube, and the second lumen extending from the proximal end of said elongated tube to a second opening at approximately the distal end of said first cylindrical portion, wherein the improvement comprises;

said elongated tube having at its distal end a smooth conical tapered tip that smoothly merges with a second cylindrical portion of said elongated tube, and said second cylindrical portion enclosing the first lumen from the conical tapered tip to approximately the location of said second opening, said second cylindrical portion having a diameter substantially greater than one-half but substantially less than a full diameter of said first cylindrical portion, said divider in said first cylindrical portion being planar, the lumens being "D" shaped in cross-section in said first cylindrical portion, the elongated tube being provided with a plurality of holes in the region of the conical tapered tip, and said first cylindrical portion of the elongated tube smoothly merging with said second cylindrical portion of the elongated tube.

8. The double lumen catheter as claimed in claim 7 wherein said second opening is defined by a bevel rising at its distal end from the planar divider and terminating at its proximal end on the outer periphery of the first cylindrical portion.

* * * * *